United States Patent
Moore et al.

(10) Patent No.: US 10,006,393 B2
(45) Date of Patent: Jun. 26, 2018

(54) METHODS AND SYSTEMS FOR DETERMINING AND REPORTING A REMAINING USEFUL LIFE OF AN AIR FILTER

(71) Applicant: GM GLOBAL TECHNOLOGY OPERATIONS LLC, Detroit, MI (US)

(72) Inventors: Joseph K. Moore, Whitby (CA); Fahim Javid, Pickering (CA); Lei Li, Whitby (CA)

(73) Assignee: GM GLOBAL TECHNOLOGY OPERATIONS LLC, Detroit, MI (US)

( * ) Notice: Subject to any disclaimer, the term of this patent is extended or adjusted under 35 U.S.C. 154(b) by 219 days.

(21) Appl. No.: 15/004,780

(22) Filed: Jan. 22, 2016

(65) Prior Publication Data

US 2017/0211498 A1 Jul. 27, 2017

(51) Int. Cl.
| | | |
|---|---|---|
| *G01M 15/05* | (2006.01) | |
| *F02D 41/22* | (2006.01) | |
| *F02D 41/26* | (2006.01) | |
| *F02M 35/024* | (2006.01) | |
| *F02M 35/10* | (2006.01) | |
| *G01N 15/08* | (2006.01) | |
| *F02M 35/09* | (2006.01) | |

(52) U.S. Cl.
CPC ............. *F02D 41/22* (2013.01); *F02D 41/26* (2013.01); *F02M 35/024* (2013.01); *F02M 35/09* (2013.01); *F02M 35/1038* (2013.01); *G01N 15/082* (2013.01); *G01N 2015/084* (2013.01)

(58) Field of Classification Search
USPC ................ 73/114.31, 114.32, 114.33, 114.37
See application file for complete search history.

(56) References Cited

U.S. PATENT DOCUMENTS

| | | | |
|---|---|---|---|
| 8,626,456 B2 | 1/2014 | Moore et al. | |
| 2011/0197580 A1* | 8/2011 | Andrasko | ............... F02D 23/00 60/602 |

* cited by examiner

*Primary Examiner* — Eric S McCall
(74) *Attorney, Agent, or Firm* — Lorenz & Kopf, LLP

(57) ABSTRACT

Methods and systems are provided for monitoring an air filter. In one embodiment, a method includes: receiving data indicating a vehicle condition; selectively computing a use life of the air filter based on pressure data and the received data; and selectively generating at least one of a notification signal and a notification message based on the use life.

19 Claims, 6 Drawing Sheets

METHODS AND SYSTEMS FOR DETERMINING AND REPORTING A REMAINING USEFUL LIFE OF AN AIR FILTER

TECHNICAL FIELD

The present disclosure generally relates to filters, and more particularly relates to methods and systems for determining and reporting a remaining useful life of an air filter.

BACKGROUND

Air filters filter particulate matter out of an air stream. For example, air filters for an engine filter particulate matter prior to the air's introduction into the combustion chamber. Over time the particulate matter accumulates and clogs the filter. A clogged air filter may lead to inefficient operation of the engine and should be replaced.

Such air filters have historically been monitored in an indirect manner to determine when they should be replaced. For example, the number of miles driven by a vehicle since its last air filter replacement is commonly used as a means for determining when it is time to replace the air filter. Using miles driven as a basis for making this determination relies on a correlation between the miles driven by the vehicle and the rate at which the vehicle's air filter clogs with particulates.

Although such a method of determining when to replace a vehicle's air filter is adequate, there is room for improvement. Accordingly, it is desirable to provide methods and systems for determining a remaining useful life of an air filter. It is further desirable to provide methods and systems reporting the remaining useful life to a user. Furthermore, other desirable features and characteristics of the present invention will become apparent from the subsequent detailed description of the invention and the appended claims, taken in conjunction with the accompanying drawings and this background of the invention.

SUMMARY

Methods and systems are provided for monitoring an air filter. In one embodiment, a method includes: receiving data indicating a vehicle condition; selectively computing a use life of the air filter based on pressure data and the received data; and selectively generating at least one of a notification signal and a notification message based on the use life.

In one embodiment, a system includes a first module that, by a processor, receives data indicating a vehicle condition, and that selectively computes a use life of the air filter based on pressure data and the received data. The system further includes a second module that, by a processor, selectively generates at least one of a notification signal and a notification message based on the use life.

DESCRIPTION OF THE DRAWINGS

The present disclosure will hereinafter be described in conjunction with the following drawing figures, wherein like numerals denote like elements, and.

DETAILED DESCRIPTION

Figure 1:
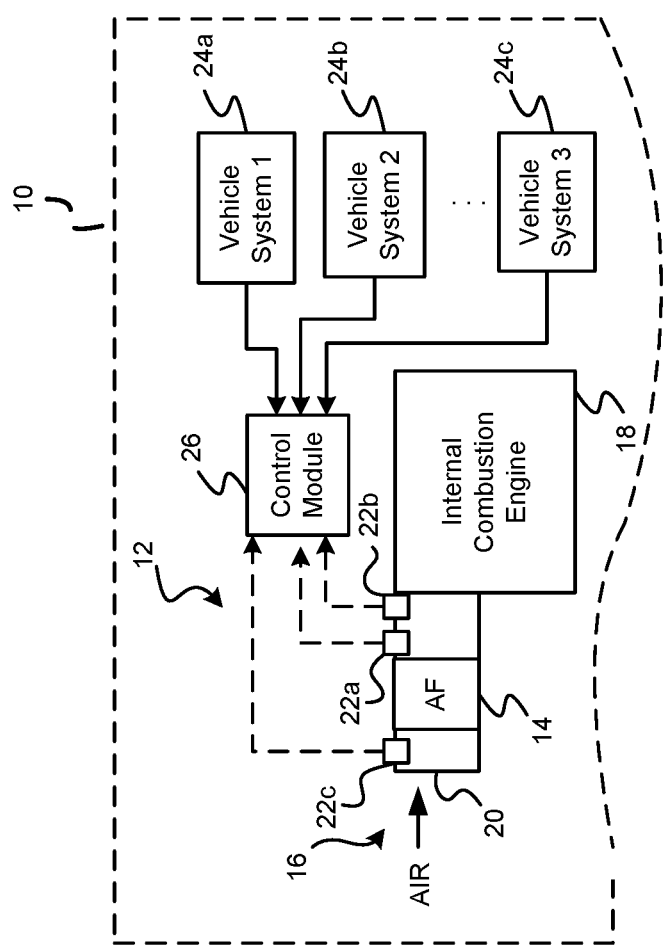
FIG. 1 is an illustration of a part of a vehicle that includes, among other features, an air filter monitoring system in accordance with various exemplary embodiments.

The following detailed description is merely exemplary in nature and is not intended to limit the application and uses. Furthermore, there is no intention to be bound by any expressed or implied theory presented in the preceding technical field, background, brief summary or the following detailed description. It should be understood that throughout the drawings, corresponding reference numerals indicate like or corresponding parts and features. As used herein, the term module refers to an application specific integrated circuit (ASIC), an electronic circuit, a processor (shared, dedicated, or group) and/or memory that executes or stores one or more software or firmware programs, a combinational logic circuit, and/or other suitable components that provide the described functionality.

Embodiments of the invention may be described herein in terms of functional and/or logical block components and various processing steps. It should be appreciated that such block components may be realized by any number of hardware, software, and/or firmware components configured to perform the specified functions. For example, exemplary embodiments may employ various integrated circuit components, e.g., memory elements, digital signal processing elements, logic elements, look-up tables, or the like, which may carry out a variety of functions under the control of one or more microprocessors or other control devices. In addition, those skilled in the art will appreciate that exemplary embodiments may be practiced in conjunction with any number of control systems, and that the vehicle systems described herein are merely exemplary embodiments.

For the sake of brevity, conventional techniques related to signal processing, data transmission, signaling, control, and other functional aspects of the systems (and the individual operating components of the systems) may not be described in detail herein. Furthermore, the connecting lines shown in the various figures contained herein are intended to represent example functional relationships and/or physical couplings between the various elements. It should be noted that many alternative or additional functional relationships or physical connections may be present in various embodiments.

Referring now to FIG. 1, a part of a vehicle 10 is shown to include an air filter monitoring system 12 that monitors an air filter 14 of an air cleaner assembly 16, among other components, of the vehicle 10 in order to predict and notify a user of a use life of the air filter 14. Although the figures shown herein depict an example with certain arrangements of elements, additional intervening elements, devices, features, or components may be present in an actual embodiments. It should also be understood that FIG. 1 is merely illustrative and may not be drawn to scale.

As depicted in FIG. 1, the vehicle 10 generally includes the air cleaner assembly 16 that includes the air filter 14. As can be appreciated, the vehicle 10 may be any vehicle type including an automobile, an aircraft, a train, a watercraft, or any other vehicle type that includes an air filter 14. For exemplary purposes, the disclosure will be discussed in the context of the vehicle 10 being an automobile having an air filter 14 associated with an engine 18 of the automobile.

In operation, the air cleaner assembly 16 is configured to take air in through an inlet 20 and to direct the air to flow through the air filter 14 and then on to the engine 18. One or more sensors referred to generally as 22 sense observable conditions of the air cleaner assembly 16 and/or the vehicle 10 and generate sensor signals based thereon. One or more vehicle systems referred to generally as 24 determine a condition associated with the vehicle 10 and generate signals and/or messages based thereon.

A control module 26 receives the signals from the sensors 22 and the signals and/or messages from the vehicle systems 24 and determines the use life of the air filter 14. The control module 26 selectively notifies a user of the use life and/or when the air filter 14 should be changed. The control module 26 notifies the user through visual, audible, and/or haptic feedback within the vehicle 10 and/or messages sent to remote devices (i.e., email messages, text messages, etc.). In various embodiments, the control module 26 further determines a peak engine power loss due to the pressure based use life of the air filter 14 and selectively notifies the user of the peak engine power loss. The control module 26 notifies the user through visual, audible, and/or haptic feedback within the vehicle and/or messages sent to remote devices (i.e., email messages, text messages, etc.).

In various embodiments, the sensors 22 can include an air pressure sensor 22a, a mass airflow sensor 22b, and an intake air temperature sensor 22c. As can be appreciated, one or more of the sensors may be combined into a single sensor (i.e., the air pressure sensor 22a and the mass airflow sensor 22b) or implemented as separate sensors (as shown). The air pressure sensor 22a and the mass airflow sensor 22b are positioned within the air cleaner assembly 16 at a location downstream of the air filter 14. The air pressure sensor 22a senses the air pressure of the air flowing from the air filter 14 and generates sensor signals based thereon. The mass airflow sensor 22b senses the flow of air from the air filter 14 and generates sensor signals based thereon.

The intake air temperature sensor 22c can be positioned within the air cleaner assembly 16 or other locations within the air cleaner assembly 16 of the vehicle 10 at a downstream of the air filter 14. The intake air temperature sensor 22c senses a temperature of the air entering the engine 18 and generates sensor signals based thereon.

In various embodiments, the one or more vehicle systems 24 generate signals and/or messages indicating conditions of the vehicle 10. The vehicle systems 24 provide the signals and/or messages directly or indirectly through a communication bus (not shown) or other communication means. The conditions can include, for example, but are not limited to, a presence of snow or rain, a condition of a system associated with snow or rain, a time of day or year, and a state or condition of an active aerodynamic system of the vehicle. The one or more vehicle systems 24 can include, but are not limited to, a windshield wiper system, a global positioning system, a vehicle calendar information system, one or more active aerodynamic systems, etc. The control module 26 uses the signals and/or messages indicating the vehicle conditions to adjust the determination of the use of life.

Figure 2:
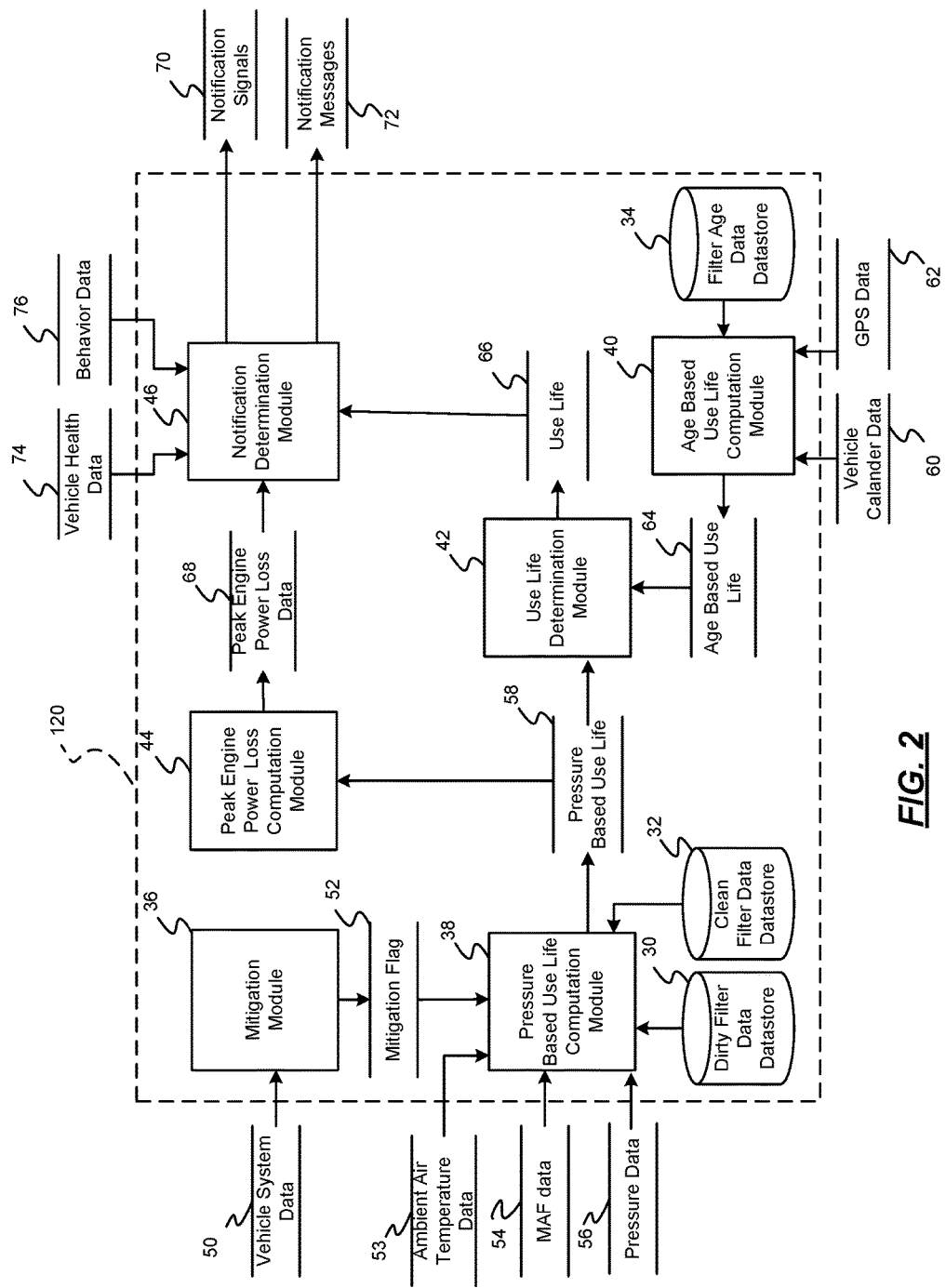
FIG. 2 is a data flow diagram of a control module of the air filter monitoring system in accordance with various exemplary embodiments.

Referring now to FIG. 2 and with continued reference to FIG. 1, a dataflow diagram illustrates various embodiments of the control module 26 in greater detail. Various embodiments of the control module 26 according to the present disclosure may include any number of sub-modules. As can be appreciated, the sub-modules shown in FIG. 2 may be combined and/or further partitioned to similarly monitor the air filter 14. Inputs to the control module 26 may be received from the sensors 22, received from the vehicle systems 24, received from other control modules (not shown) of the vehicle 10, and/or determined by other sub-modules (not shown) of the control module 26. In various embodiments, the control module 26 includes a dirty filter data datastore 30, a clean filter data datastore 32, a filter age data datastore 34, a mitigation module 36, a pressure based use life computation module 38, an age based use life computation module 40, a use life determination module 42, a peak engine power loss computation module 44, and a notification determination module 46.

Figure 3:
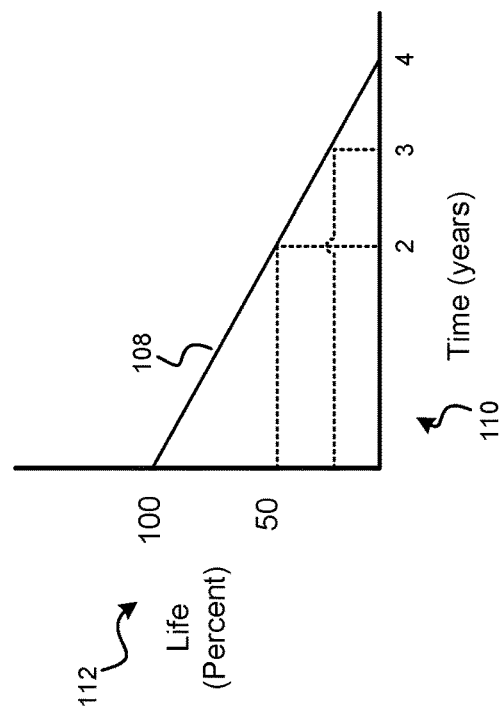
FIGS. 3, 4, and 5 are graphs illustrating data of the air filtering monitoring system in accordance with various exemplary embodiments.

The dirty filter data datastore 30 stores pressure data corresponding to a dirty air filter. The data may be determined based on an average (or other value) of measurements taken from a dirty filter (e.g., a filter mostly covered in particulate). The pressure data can be stored in one or more interpolated lookup tables. In various embodiments, a lookup table is indexed by mass airflow. In such embodiments, the pressure data stored in the lookup table indicates a pressure value for a dirty air filter at a particular mass airflow value. As shown in FIG. 3, the pressure data and mass airflow data can correspond to a curve 100, where the x-axis 102 represents mass airflow and the y-axis 104 represents a pressure value.

In various embodiments, the dirty filter data datastore 30 can store multiple lookup tables. In such embodiments, each lookup table may correspond to a particular intake air temperature or a range of intake air temperatures. In various other embodiments, the lookup table may be a two-dimensional look up table that is indexed by mass airflow and intake air temperature.

With reference back to FIG. 2, the clean filter data datastore 32 stores pressure data corresponding to a clean air filter. The data may be determined based on an average (or other value) of measurements taken from a clean filter (e.g., a new filter). The pressure data can be stored in one or more interpolated lookup tables. In various embodiments, a lookup table is indexed by mass airflow. In such embodiments, the pressure data indicates a pressure value (in kPa) for a clean air filter at a particular mass airflow value (in Kg/s). As shown in FIG. 3, the pressure data and mass airflow data can correspond to a curve 106, where the x-axis 102 represents mass airflow and the y-axis 104 represents a pressure.

In various embodiments, the clean filter data datastore 32 can store multiple lookup tables. In such embodiments, each lookup table may correspond to a particular intake air temperature or a range of intake air temperatures. In various other embodiments, the lookup table may be a two-dimensional look up table that is indexed by mass airflow and intake air temperature.

Figure 4:
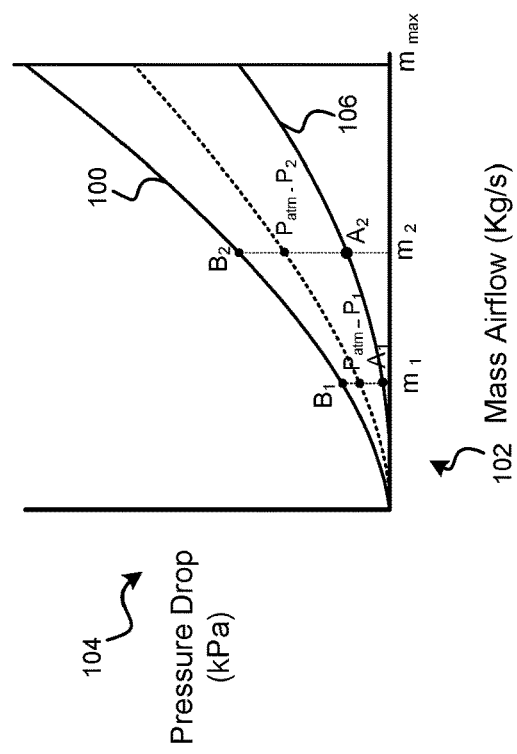

The filter age data datastore 34 stores estimated life data for an average filter. The data may be determined based on an average (or other value) of air filters. The life data can be stored in an interpolated lookup table. In various embodiments, the lookup table is indexed by age. In such embodiments, the life data indicates a life value (in percent) for an air filter at a particular age (in years). As shown in FIG. 4, the life data and age data can correspond to a curve 108, where the x-axis 110 represents age and the y-axis 112 represents life.

With reference back to FIG. 2, the mitigation module 36 receives as input vehicle system data 50. The vehicle system data 50 can be generated by the vehicle systems 24 and can be used to determine a state or condition of a vehicle system that may affect air pressure within the air cleaner assembly 16. For example, the vehicle system data 50 can include data that indicates a presence of rain or snow on a windshield (e.g., from a rain sensor), an operation status of a windshield wiper (e.g., from a windshield wiper system), or current weather conditions (e.g., from GPS). The mitigation module 36 evaluates the vehicle system data 50 to determine when rain or snow may be accumulating on the air filter. The mitigation module 36 then controls when to and when not to evaluate the pressure in the air filter assembly based on the determined presence of rain or snow. For example, the mitigation module 36 can generate a mitigation flag 52 that indicates to not evaluate the pressure data based on the presence of rain or snow. In another example, the mitigation module 36 can change the status of the mitigation flag 52 to indicate to evaluate the pressure data when it has determined the presence of rain or snow on the filter is gone (e.g., through evaporation from engine heat or some other method).

In another example, the vehicle system data 50 can include data that indicates a status or condition of an active aerodynamic system that affects the airflow into the air cleaner assembly 16 (e.g., a shutter status, or other condition). The mitigation module 36 evaluates the vehicle system data 50 to determine when air is the influence of airflow into the air cleaner assembly 16. The mitigation module 36 then controls when to and when not to evaluate the pressure in the air filter assembly based on the determined presence influence of airflow into the air cleaner assembly 16. For example, the mitigation module 36 can generate a mitigation flag 52 that indicates to not evaluate the pressure data based on the influence of airflow. In another example, the mitigation module 36 can change the status of the mitigation flag 52 to indicate to evaluate the pressure data when it has determined the influence of airflow has changed.

The pressure based use life computation module 38 receives as input the mitigation flag 52, intake air temperature data 53, mass airflow data 54, and pressure data 56. The intake air temperature data 53 can be based on the sensor signals received from the intake air temperature sensor 22c. The mass airflow data 54 may be based on the sensor signals received from the mass airflow sensor 22b. The pressure data 56 may be based on the sensor signals received from the air pressure sensor 22a. For example, with particular reference to the graph shown in FIG. 3, the mass airflow data 54 includes a mass airflow value ($m_1$) sensed at a first time when the mass airflow is expected to be low; and the pressure data 56 includes a pressure ($P_1$) sensed at the first time when the airflow is expected to be low. The mass airflow data further includes a mass airflow ($m_2$) sensed at a second time when the mass airflow is expected to be high; and the pressure data further includes a pressure ($P_2$) sensed at the second time when the airflow is expected to be high As used herein, the terms "high" and "low" are relative terms meaning that the high airflow rate must be higher than the low airflow rate and the low airflow rate must be lower than the high airflow rate. In various embodiments, the sequence of such measurements may be irrelevant. For example, the two air pressure measurements may be referred to herein as "paired data." The two pressure measurements in each set of paired data can be taken within a predetermined period of time of one another to minimize errors that might otherwise result from changing atmospheric pressure due to changing weather conditions, changing elevations, changing geographic location, or other factors. The length of the predetermined period of time may vary depending on geographical, seasonal, and/or other considerations. For example, the predetermined period of time may be less than or equal to about 2-30 seconds.

Additionally, each measurement is generally not taken until after the air flow has reached a steady state condition. As used herein, the term "steady state condition" in connection with air flow refers to a condition where fluctuations in air flow do not exceed a predetermined value. In some examples, it may be desirable to set the predetermined value for fluctuations in the air flow rate at less than or equal to approximately 1-20 grams/second.

The pressure based use life computation module 38 computes a use life 58 based on the mass airflow data 54, the pressure data 56, and the pressure data stored in the clean filter data datastore 32 and the dirty filter data datastore 30. For example, with reference to FIG. 3, the pressure based use life computation module 38 retrieves from the dirty filter data datastore 30 a first pressure value ($B_1$) that corresponds to the mass airflow ($m_1$) on the curve 100 that is associated with the intake air temperature data 53 for the dirty filter and retrieves a second pressure value ($B_2$) that corresponds to the mass airflow ($m_2$) on the curve 100 that is associated with the intake air temperature data 53 for the dirty filter. The pressure based use life computation module 38 retrieves from the clean filter data datastore 32 a first pressure value ($A_1$) that corresponds to the mass airflow ($m_1$) on the curve 106 that is associated with the intake air temperature data 53 for the clean filter and retrieves a second pressure value ($A_2$) that corresponds to the mass airflow ($m_2$) on the curve 106 that is associated with the intake air temperature data 53 for the clean filter.

The pressure based use life computation module 38 then computes the use life 58 based on a pressure differential computed from the sensed pressure $P_1$ and sensed the pressure $P_2$, and the retrieved pressure values $A_1$, $A_2$, $B_1$, and $B_2$. For example the pressure based use life computation module computes the use life 58 based on the following equation:

$$UL1(\%) = 100 \times \frac{(B2 - B1) + (P2 - P1)}{(B2 - A2) - (B1 - A1)}. \quad (1)$$

The age based use life computation module 40 receives as input vehicle calendar data 60, and/or GPS data 62. The age based use life computation module 40 computes an age of the air filter based on the vehicle calendar data 60 and/or the GPS data 62. For example, the age based use life computation module 40 determines the age from an identified last filter change (i.e., from a user initiated signal or other signal identifying a filter change) using calendar data indicating days and/or GPS data indicating a current day or time. The age based use life computation module 40 then determines a use life 64 based on the age. For example, as shown in greater detail with regard to FIG. 4, the age based use life computation module 40 retrieves from the filter age data datastore 34 a use life (in percent) that corresponds to the determined age (in years). The age based use life 64 is set equal to the retrieved value.

The use life determination module 42 receives as input the pressure based use life 58 and the age based use life 64. The use life determination module 42 determines an actual use life 66 based on the pressure based use life 58 and the age based use life 64. For example, the use life determination module 42 determines the actual use life 66 based on a minimum of the pressure based use life 58 and the age based use life 64.

The peak engine power loss computation module 44 receives as input the pressure based use life 58 computed in equation 1. The peak engine power loss computation module computes the peak engine power loss based on the pressure based use life 58. For example, the peak engine power loss computation module 44 computes the peak engine power loss based on the following equation:

$$\text{Peak Engine Power Loss} = (\text{Peak Engine Power}) * (0.01250) * (2.5) * (100 - UL1)/100.$$

The notification determination module 46 receives as input the actual use life 66 and the peak engine power loss data 68. The notification determination module 46 generates notification signals 70 and/or notification messages 72 to notify the user based on the use life 66 and/or the peak engine power loss data 68.

In various embodiments, the notification determination module 46 generates the notification signals 70 and/or messages 72 when the use life 66 indicates that the life of the air filter 14 is near complete (e.g., when the use life 66 is less than a threshold). The notification signals 70 and/or messages 72 include a message or other indication (e.g., audio or haptic) that the life of the air filter is near complete or that it is time to change the air filter 14.

In various embodiments, the notification determination module 46 generates the notification signals 70 and/or messages 72 at a time that may be more convenient for the user. For example, the notification determination module 46 may receive as input vehicle health data 74 and/or behavior data 76. The notification determination module 46 coordinates the delivery and/or content of the notification signals 70 and/or messages 72 based on the vehicle health data 74 and/or the behavior data 76.

For example, the vehicle health data 74 includes health information about other vehicle components. The notification determination module 46 coordinates the delivery of the notification signals 70 and/or messages 72 with signals and/or messages that may be delivered based on the health of the other vehicle components. For example, the vehicle health data 74 can include a health of the engine oil (e.g., oil life). In such example, the notification determination module 46 coordinates the delivery of the notification signals 70 and/or messages 72 with notification signals and/or messages associated with the engine oil. For example, the notification determination module 46 tracks the use life 66 and an estimated engine oil life and once the use life falls below a threshold, generates the notification signals 70 and/or messages 72, at a same time that notification signals and/or messages are to be generated for the engine oil. As can be appreciated, the engine oil life is one example, as other vehicle health data can be used to coordinate the delivery and/or content of the notification signals 70 and/or messages 72 as the disclosure is not limited to the present examples.

Figure 5:
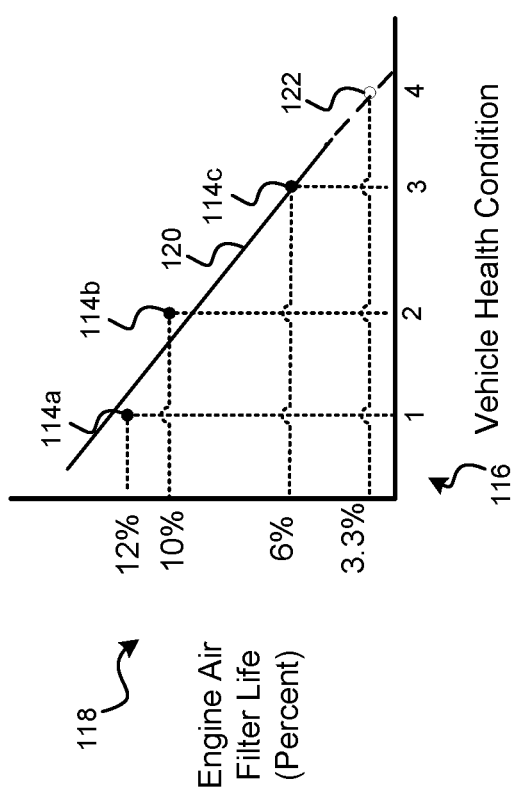

In another example, the behavior data 76 includes previously determined use lives at previous maintenance events. The notification determination module can adjust the threshold for generating the notification signals and/or messages based on the previously determined use lives at the previous maintenance events. For example, as shown in FIG. 5, the behavior data is shown at 114a-114c, where the x-axis 116 represents a vehicle health condition such as oil change events and the y-axis 118 represents air filter use life (in percent). The behavior data 114-114c can be used to establish a linear regression line 120. The linear regression line 120 is then used to predict an air filter use life 122 at a predicted next maintenance event. The threshold described above can be adjusted if the predicted air filter use life 122 is not below zero (or other number) before the next predicted maintenance event. As can be appreciated, other maintenance behavior can be used to modify the threshold as the disclosure is not limited to the present examples.

Figure 6:
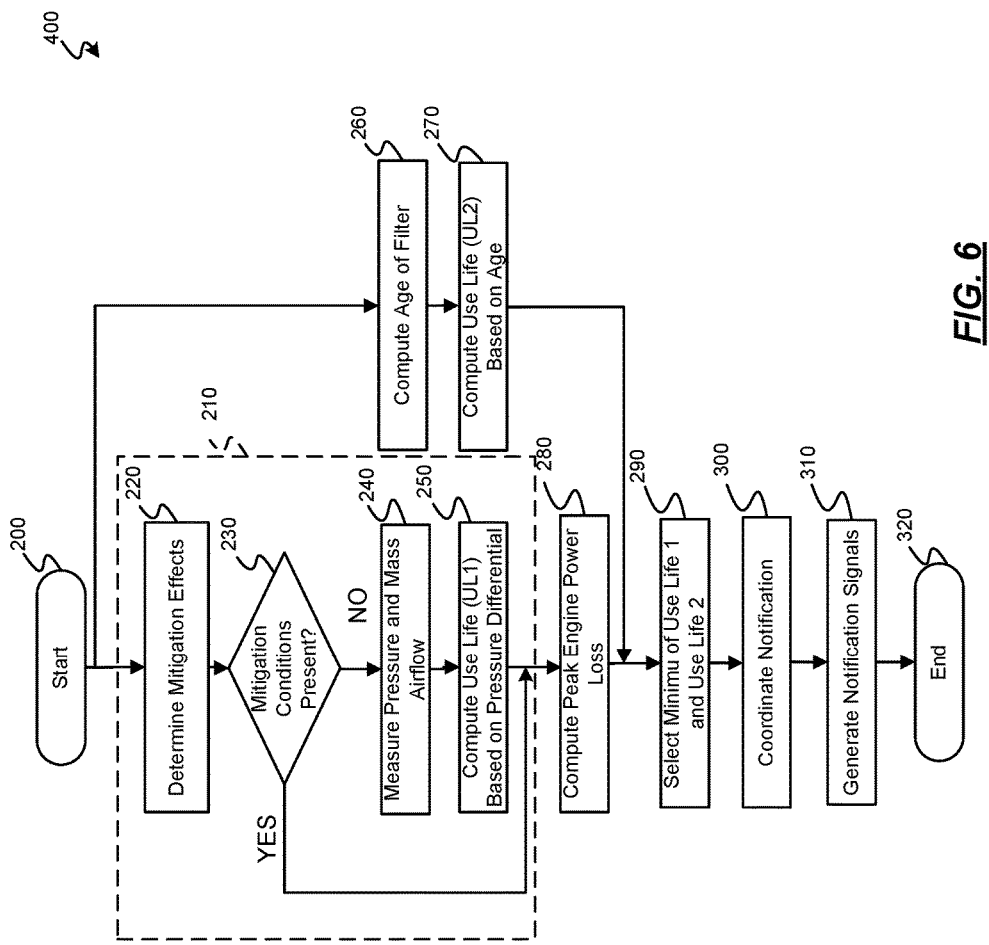
FIGS. 6 and 7 are flowcharts illustrating methods for monitoring an air filter of a vehicle in accordance with various exemplary embodiments.
Figure 7:
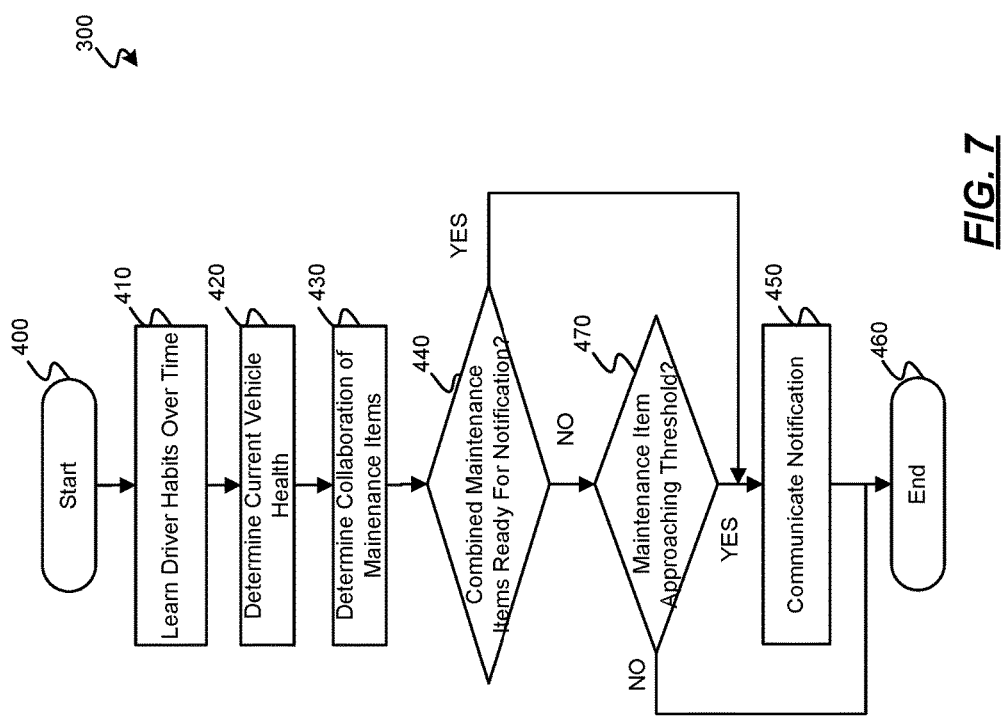

Referring now to FIGS. 6 and 7, and with continued reference to FIGS. 1-5, flowcharts illustrate methods that can be performed by the air filter monitoring system 12 in accordance with various embodiments. As can be appreciated in light of the disclosure, the order of operation within the method is not limited to the sequential execution as illustrated in FIGS. 6 and 7, but may be performed in one or more varying orders as applicable and in accordance with the present disclosure.

As can further be appreciated, the methods of FIGS. 6 and 7 may be scheduled to run at predetermined time intervals during operation of the vehicle 10 and/or may be scheduled to run based on predetermined events.

In one example, as shown in FIG. 6, the method may begin at 200. The pressure based use life 58 is computed based on the pressure drop at 210. For example, the vehicle conditions such as, but not limited to rain, snow, active aerodynamic conditions, etc. are evaluated to determine whether mitigation conditions are present at 220. If it is determined that mitigation conditions are present 230, then the pressure data is not evaluated and the method continues to step 280 where the peak engine power loss is computed based on a previously computed pressure based use life 58.

If it is determined that mitigation conditions are not present at 230, the use life 66 is determined at 240-250. For example, at 240 the air pressure ($P_1$) and the mass air flow ($m_1$) at a first time are received and within a predetermined period of time, the air pressure ($P_2$) and the mass air flow ($m_2$) at a second time are received. The pressure based use life 58 is then computed based on equation (1) above and the dirty filter data and the clean filter data retrieved from the dirty filter data datastore and the clean filter data datastore, respectively based on the intake air temperature. Thereafter, the peak engine power loss is computed based on the computed pressure based use life 58 at 280.

Meanwhile, at 260-270, the age based use life 64 is computed based on an estimated age of the air filter 14. For example, the age of the air filter 14 is computed for example based on the vehicle calendar data 60 and/or the GPS data 62 at 260 and the use life 64 is determined based on the age and the filter age data stored in the filter age data datastore 34 at 270.

At 290, the actual use life 66 is determined from minimum of the pressure based use life 58 and the age based use life 64 at 280. The peak engine power loss data 68 is determined at 290. The notification signals 70 and/or messages 72 are coordinated at 300 and if it is time for a notification, the notification signals 70 and/or messages 72 are generated at 310. Thereafter, the method may end at 320.

In another example, a method 300 of coordinating the notification signals 70 and/or messages 72 is shown in FIG. 7. The method may begin at 400. Driver behavior, such as when a driver brings the vehicle 10 in for service is learned at 410. The current vehicle health is determined at 420. Based on the behavior and the current vehicle health, a collaboration of maintenance items is determined at 430. For example, as discussed above maintenance items such as engine oil changes and the air filter change is coordinated based on the use life 66.

If it is determined that combined maintenance items require notification at 440, notification signals 70 and/or messages 72 are generated at 450 and the method may end at 460. If it is determined that combined maintenance items do not need notification at 440; however, one of the maintenance items is approaching or has exceeded a threshold limit at 470, the notification signal 70 and/or the messages 72 are generated at 450 and the method may end at 460.

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing the exemplary embodiment or exemplary embodiments. It should be understood that various changes can be made in the function and arrangement of elements without departing from the scope of the invention as set forth in the appended claims and the legal equivalents thereof.

What is claimed is:

1. A method of monitoring an air filter, the method comprising:
    receiving data indicating a vehicle condition, wherein the received data indicates at least one of a wiper blade condition, a rain sensor condition, and a weather condition;
    determining a presence of snow or rain on the air filter based on the received data;
    receiving pressure data associated with airflow downstream of the air filter;
    selectively computing a use life of the air filter based on the pressure data and the determination of the presence of snow or rain on the air filter; and
    selectively generating at least one of a notification signal and a notification message based on the use life.

2. The method of claim 1, further comprising selectively obtaining the pressure data based on the presence of snow or rain on the air filter.

3. The method of claim 1, wherein the received data indicates an active aerodynamic condition, and wherein the method further comprises determining an influence of airflow into an air cleaner assembly based on the aerodynamic condition.

4. The method of claim 3, further comprising selectively obtaining the pressure data based on the influence of airflow into the air cleaner assembly.

5. The method of claim 1, wherein the computing the use life is based on sensed pressure data and pressure data associated with a dirty filter.

6. The method of claim 5, wherein the received data indicates intake air temperature, and wherein the pressure data associated with the dirty filter is adjusted based on the intake air temperature.

7. The method of claim 1, wherein the computing the use life is based on sensed pressure data and pressure data associated with a clean filter.

8. The method of claim 7, wherein the received data indicates intake air temperature, and wherein the pressure data associated with the clean filter is adjusted based on the intake air temperature.

9. The method of claim 1, further comprising selectively computing a second use life of the air filter based on filter age data, and wherein the selectively generating the at least one of notification signal and notification message is based on at least one of the use life and the second use life.

10. The method of claim 1, wherein the selectively generating the at least one of notification signal and notification message is based on learned maintenance behavior.

11. The method of claim 1, wherein the selectively generating the at least one of notification signal and notification message is based on a current vehicle oil life.

12. A system for monitoring an air filter, the system comprising:
    a first module that, by a processor, receives pressure data associated with air flow downstream of the air filter, receives data indicating a vehicle condition, wherein the received data indicates at least one of a wiper blade condition, a rain sensor condition, and a weather condition, determines a presence of snow or rain on the air filter based on the received data and selectively computes a use life of the air filter based on the pressure data and the determination of the presence of snow or rain on the air filter; and
    a second module that, by a processor, selectively generates at least one of a notification signal and a notification message based on the use life.

13. The system of claim 12, wherein the first module obtains the pressure data based on the presence of snow or rain on the filter.

14. The system of claim 12, wherein the received data indicates an active aerodynamic condition, and wherein first module determines an influence of airflow into an air cleaner assembly based on the aerodynamic condition.

15. The system of claim 14, wherein the first module selectively obtains the pressure data based on the influence of airflow into the air cleaner assembly.

16. The system of claim 12, wherein the first module computes the use life based on sensed pressure data and pressure data associated with at least one of a dirty filter and a clean filter.

17. The system of claim 16, wherein the received data indicates intake air temperature, and wherein the pressure data associated with the at least one of dirty filter and clean filter is adjusted based on the intake air temperature.

18. The system of claim 12, wherein the second module selectively generates the at least one of notification signal and notification message based on learned maintenance behavior.

19. The system of claim 12, wherein the second module selectively generates the at least one of notification signal and notification message based on a current vehicle oil life.

* * * * *